United States Patent
Huang et al.

(10) Patent No.: US 9,434,705 B2
(45) Date of Patent: Sep. 6, 2016

(54) L-SETASTINE HYDROCHLORIDE AND PREPARATION METHOD THEREOF

(75) Inventors: Qingyun Huang, Hefei (CN); Qingguo Huang, Hefei (CN); Meixian Lou, Hefei (CN)

(73) Assignee: ANHUI QINGYUN PHARMACEUTICAL & CHEMICAL CO., LTD., Hefei, Anhui (CN)

( * ) Notice: Subject to any disclaimer, the term of this patent is extended or adjusted under 35 U.S.C. 154(b) by 126 days.

(21) Appl. No.: 14/358,229

(22) PCT Filed: Jul. 10, 2012

(86) PCT No.: PCT/CN2012/078434
§ 371 (c)(1),
(2), (4) Date: May 15, 2014

(87) PCT Pub. No.: WO2013/075510
PCT Pub. Date: May 30, 2013

(65) Prior Publication Data
US 2014/0296517 A1    Oct. 2, 2014

(30) Foreign Application Priority Data

Nov. 21, 2011  (CN) .......................... 2011 1 0372464

(51) Int. Cl.
*C07D 223/04* (2006.01)
*C07D 295/088* (2006.01)
*A61K 31/55* (2006.01)

(52) U.S. Cl.
CPC ........... *C07D 295/088* (2013.01); *A61K 31/55* (2013.01)

(58) Field of Classification Search
CPC ..................................................... C07D 223/04
USPC ........................................................ 540/609
See application file for complete search history.

(56) References Cited

FOREIGN PATENT DOCUMENTS

CN           101486687 A   *   7/2009

* cited by examiner

*Primary Examiner* — Brenda Coleman
(74) *Attorney, Agent, or Firm* — Raymond Y. Chan; David and Raymond Patent Firm

(57) ABSTRACT

The present invention relates to the field of medicine, and disclosed are an L-setastine hydrochloride and a preparation method therefor. The compound of the present invention has the advantages of stronger histamine Hi receptor antagonism and small side effect; the yield of the preparation method is more than 80%, and the product purity is high. The present invention also provides an application of the compound as an H1 histamine receptor antagonist.

10 Claims, No Drawings

L-SETASTINE HYDROCHLORIDE AND PREPARATION METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to the field of medicines and more particularly to a compound of L-setastine hydrochloride and a preparation method therefor.

2. Description of Related Arts

The most common allergic diseases include asthma, allergic rhinitis, hives, allergic dermatitis, and drug allergies, etc., and these common allergic diseases are the major reasons for causing the death of human. Due to the increase of aging population and serious environmental pollutions, the incidence of allergic diseases will be dramatically increased, thereby seriously threatening to the health of the human. The main reason for the incentive of allergic diseases is due to the excitement caused by histamine HI receptors, and therefore, the scientists keep working on research antagonist drugs for HI histamine receptor.

Currently, in clinical application, the most common antihistamine HI receptor drugs are chlorpheniramine, astemizole, terfenadine, clemastine fumarate, cetirizine hydrochloride and loratadine. Chlorpheniramine has strong sedative side effects, and weak antihistamine effects. The sedative side effects of astemizole and terfenadine are relatively weak, and the onsets thereof are slow, and then the cardiac side effects thereof are strong, so that the practical use of astemizole and terfenadine are stopped by many countries. Clemastine fumarate is an anti-allergy drug, and the anti-cold non-prescription medicines with the compound of clemastive fumarate are on the top three sales in United States. However, the synthesis process of clemastive fumarate is complicated, and key intermediates for synthesizing the clemastive fumarate have to be imported, so that the manufacturing cost is too high to industrial production.

However, the sedative side effects of cetirizine hydrochloride are small, but overdose of cetirizine hydrochloride may cause fatal arrhythmias. Because of complex synthetic process of cetirizine hydrochloride, the crystallizations of the products with cetirizine hydrochloride are difficult. Although, a lot of manufacturer produces cetirizine hydrochloride medicines, but it is difficult to achieve the industrial production. Loratadine has efficiency treatment effects and low in side effects, but the synthesis process thereof is also complicated and high in cost, so that it is difficult for industrial productions.

Setastine hydrochloride is an HI-receptor antagonists with efficient in treatment and low toxicity, and it can inhibit histamine-induced bronchial spasms of guinea pigs. The efficacy time of setastine hydrochloride is longer than that of clemastine. In addition, setastine hydrochloride has no anticholinergic and anti-5-serotonin effect after using, and no effects on the cardiovascular system. In other words, it has the same selectivity effects for peripheral H1-receptor as non-sedating antihistamine loratadine.

Comparing with other existing antagonist drug for HI histamine receptors, setastine hydrochloride has the following advantages of:

1. having strong anti-histamine effects, having rapid onset times within 30 minutes after taking, small and slight in side effects, no cardiac side effects, and relieving symptoms for patients having pruritus diseases and resisting to other antihistamines medicines.

2. having small in dose. It is selective to adjust the dosage for using setastine hydrochloride according to the severity of allergy. The dosage thereof is only 1~4 mg daily. In other words, it has a widely secure daily dosage, which is sixtieth of the daily dosage of terfenadine.

3. having simple in synthesis steps, low in cost, and being able to produce in the to laboratory scale. The cost for producing per kilogram of setastine hydrochloride is the same as that of terferadine. That is to say, in the economic field, setastine hydrochloride has significant advantages comparing with other similar drugs.

Accordingly, setastine hydrochloride was listed in 1987 in Hungary, and was listed in China market after 1987. It was listed in racemic drugs to the China market, and show that it has stronger sedative side effects in clinical use.

SUMMARY OF THE PRESENT INVENTION

A main object of the present invention is to provide a L-setastine hydrochloride, which is a strong histamine HI receptor antagonist and has small in side effects, wherein the chemical name of L-setastine hydrochloride is (R)-(−)-1-[2-[1-(4-chlorophenyl)-1-ethoxyphenyl]hexahydro-1H-azepine, which is L-setastine hydrochloride. The structural formula of L-setastine hydrochloride shows as follow:

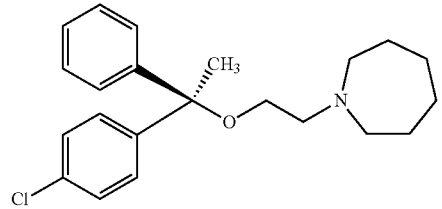

Formula I

The present inventors have found that D-setastine hydrochloride has no antihistaminic effect, but it can produce side effects of sedation.

The present invention also provides a compound and a pharmaceutically acceptable of formula I as histamine HI receptor antagonists.

According to experiments of the histamine-induced death effects for guinea pigs having L-setastine hydrochloride, which is a compound of formula I, the death percentages of high, medium, and small-dose group of D-setastine hydrochloride are 100% comparing with the blank control group, so that D-setastine hydrochloride doesn't have a protective effect for inhibiting the histamine-induced death for guinea pigs. The death percentage of high, medium, and small-dose group of L-setastine hydrochloride are 0%, 18% and 45% respectively; and the death percentages of high, medium, and small-dose group of setastine hydrochloride racemic group are 16%, 36% and 66% respectively. Therefore, D-setastine hydrochloride has no protective effect for inhibiting on histamine-induced death for guinea pigs, and L-setastine hydrochloride and setastine hydrochloride racemic have protective effects on histamine-induced death for guinea pigs, wherein the protective effects of L-setastine hydrochloride is stronger than that of setastine hydrochloride racemic.

Another object of the present invention to provide a method for preparing compounds of formula I, which is L-setastine hydrochloride, in the absence of air environment, a compound of formula II is reacted with a compound of the formula III, which is R-chlorodiphenethyl alcohol, in a solvent with a alkali-based compound below the solvent reflux temperature for 4~6 hours, so as to obtain the compound of formula I, L-setastine hydrochloride. The structural formula II and formula III shows as follow:

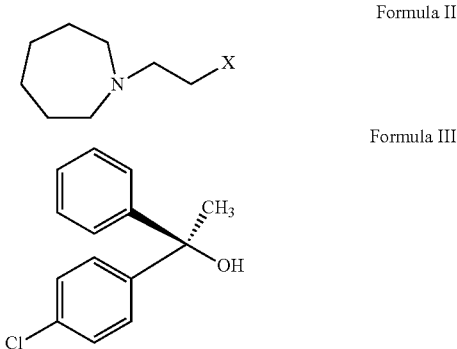

Formula II

Formula III

"X" of formula II can be Cl, Br, I, acyloxy, and sulfonyloxy, such that the formula II can be N-(2-bromoethyl) azepine cycloheptane, N-(2-bromoethyl)-azepine, and p-toluenesulfonic acid 2-aza-cyclohexyl ester.

Preferably, the solvent can be benzene, substituted benzene, alcohols, ethers, acetonitrile, haloalkane, N,N-dimethyl formamide, N,N-dimethyl acetamide, N-methyl pyrrolidone or hexamethylphosphoramide.

Preferably, the alkali-based compound can be organic base, inorganic base, and alkali metal salt. According to the preferred embodiment of the present invention, the alkali-based compound can be sodium amide, potassium tert-butoxide, sodium tert-butoxide, sodium methoxide, potassium methoxide, sodium ethoxide, potassium ethoxide, Sodium hydride, lithium hydride, potassium hydride, alkali metal hydroxides, such as sodium hydroxide, potassium hydroxide, etc., alkali metal salts, such as potassium carbonate, cesium carbonate, sodium carbonate, etc., and organic amines, such as triethylamine, pyridine, DBU, diisopropylethylamine, and tetramethylethylenediamine.

Preferably, the reaction between formula II and formula III is carried out in the presence of a catalyst. In the preferred embodiment of the present invention, the catalyst is polyethylene glycol, quaternary ammonium salt or crown ether.

The equation of the reaction shows as follow:

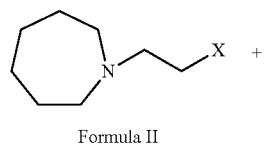

Formula II

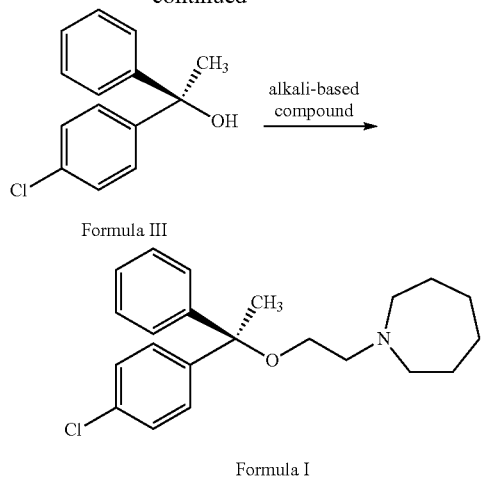

Formula III

Formula I

According to the preferred embodiment of the present invention, a preparation method about above mentioned reaction between the formula II and formula III is illustrated, wherein the final product is analyzed by NMR instrument, and the yield of the reaction therebetween is 80~85%, mp173~175° C., and ee99.0%~99.2%.

The compound of formula I can be obtained by using the SFC method. The Daicel preparation equipment and Daicel chiral column are adapted for chiral isomer separation for setastine hydrochloride racemic and collect its corresponding component, so that pure optical isomers, L-setastine hydrochloride, are obtained by rotary evaporators.

The invention also provides pharmaceutical compositions, including the compound of formula I and a pharmaceutically acceptable carrier, adjuvant, or excipient. The histamine HI receptors can be effectively detected by the composition of the present invention The compounds of the present invention is free-form, or suitable and pharmaceutically acceptable derivative thereof. According to the present invention, the pharmaceutically acceptable derivatives include, but are not limited to, pharmaceutically acceptable pro-drugs or salts thereof. The present invention can also be derivatives for direct or indirect administrations, which are required medicines for patients. In addition, the present invention also can be metabolites or residues.

According to the present invention, the present invention is a pharmaceutically acceptable composition, which can be pharmaceutically acceptable carriers, adjuvant, or excipient, such as solvents, diluents, other kinds of liquid excipient, dispersing agents, suspending agents, surface activating agents, isotonic agents, thickener, emulsifying agents, preservatives, solid binders, and lubricants, etc., which are adapted to match requirements for specific targets. Various pharmaceutically acceptable carriers can be applied to the preparation of the compositions of the present invention and their preparation methods are known in the art. In addition, any conventional carrier medium, which is incompatible with the compounds of the present invention, is also considered in the scope of the present invention.

The pharmaceutically acceptable carrier includes, but are not limited to, ion exchangers, aluminum, aluminum stearate, lecithin, serum proteins, such as human serum albumin, buffer substances, such as phosphates, glycine, sorbic acid, potassium sorbic acid, mixture of saturated and vegetable fatty acids, water, salts or electrolytes, such as protamine sulfate, disodium hydrogen phosphate, potassium dihydrogen phosphate, sodium chloride, zinc salts, colloidal silica, magnesium trisilicate, polyvinylpyrrolidone, polyacrylates, wax, polyethylene-polyoxypropylene-block polymers, lanolin, sugars, such as lactose, glucose and sucrose; starches such as corn starch and potato starch; cellulose and its derivatives, such as sodium carboxymethyl cellulose, ethyl cellulose ethoce and cellulose acetate; gum powder; malt; gelatin; talc; excipients, such as cocoa butter and suppository waxes; oils, such as peanut oil, cottonseed oil, safflower oil, sesame oil, olive oil, corn oil and soybean oil; diol compound, such as propylene glycol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethanol, phosphate buffer, and other suitable non-toxic lubricants, such as sodium laurylsulfate and magnesium stearate, coloring agents, releasing agents, clothing lining, sweetening agents, flavoring agents and spices, preservatives and antioxidants.

The compositions of the present invention may be administered orally, parenteral administration, inhalation spray administration, topical administration, rectal administration, nasal administration, sublingual administration, or administration by the implanting kit.

DETAILED DESCRIPTION OF THE PREFERRED EMBODIMENT

The following description is disclosed an L-setastine hydrochloride, and its preparation method therefore, and any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

In order to enable the person skilled in the art to better understand the technical solution of the present invention, the followings combine a preferred embodiment to further illustrate the present invention.

Embodiment 1

Preparation of Reaction Compounds

The preparation for R-chlorodiphenethyl alcohol: References documents: Angew. Chem. Int. Ed. 2007, 46, 5373-5376 or Tetrahedron Letters, Vol. 37, No. 36, pp. 6453-6456, 1996.

The preparation for N-(2-bromoethyl)azepane and p-toluene sulfonic acid 2-aza-cyclohexyl ester: Referring to Patent Document (CS 248547, 1988), the azepane and chloroethanol are refluxed in toluene for 3 hours to obtain N-(2-hydroxyethyl)azepane, and then reacts with a halogenating agent (e.g. hydrobromic acid, phosphorus tribromide, thionyl chloride, etc.) or sulfonyl chloride (such as p-toluenesulfonyl chloride, m-nitrobenzenesulfonyl chloride, etc.) so as to produce corresponding halides (such as N-(2-bromoethyl)azepane) or a sulfonate (such as p-toluene sulfonic acid 2-aza-cyclohexyl ester)

Embodiment 2

The Synthesis of L-setastine Hydrochloride

1. The 23.6 g (0.6 mole) of sodium amide and 100 ml of toluene are added in a reaction flask, and filing nitrogen gas into the reaction flask to stir at the temperature of 60~70° C. And, 50 ml of toluene solution with 51.3 g (0.3 moles) of R-chlorodiphenethyl alcohol dissolved therein are completely and dropwisely added into the reaction flask within 1 hour, and heat preservation such reaction flask with reaction solution for 2 hours. Then, 100 ml of toluene solution with 74.2 g (0.36 moles) N-(2-bromoethyl)azepane dissolved therein are completely and dropwisely added into the reaction flask at the temperature of 70~80° C., and then adding 5 grams of PEG400 therein to reflux for 5 hours and finally placed the reaction flask in the room temperature overnight.

2. The reaction flask with reaction solution as mentioned in step 1 is cooled until 0° C., and dropwisely adding 150 ml of water into the reaction flask and extracting the aqueous layer via 100 ml of toluene; and then combining the toluene layer to wash with 100 ml of ice water once time; and then drying out with anhydrous $MgSO_4$; and adding 2 g of activated carbon into the reaction flask. After decolorizing below 20° C., HCl (g) is filled into the reaction flask until pH value to 2~3 so as to generate solid precipitated, and draining out all solution and adding acetone to process recrystallization so as to generate white L-setastine hydrochloride solid with the yield of 80%. mp173~175° C., ee99.0% [chiral column: CHIRALPAK AY-H, 0.46 cm I.D.×15 cm, mobile phase: $CO_2$/EtOH/DEA=85/15/0.1 (v/v), flow rate: 2.0 ml/min, detection wavelength: UV 220 nm], $[a]_D^2=-7.6°$ (c1.00, $CH_3OH$). NMR results were as follows: ¾-NMR (DMSO-d6, δ (ppm)): 1.56-1.65 (4H), 1.82-1.87 (4H), 1.87 (3H), 3.17-3.37 (4H), 3.32 (2H), 3.60 (2H), 7.20-7.41 (9H).

Embodiment 3

The Synthesis of L-setastine Hydrochloride 1. 43.2 g (0.45 mol) of sodium tert-butoxide and 100 ml of acetonitrile are added to the reaction flask with nitrogen gas for stirring at the temperature of 70~80° C. Then, 50 ml of acetonitrile with 51.3 g (0.3 mole) of R-p-dichlorobenzene ethanol dissolved therein are dropwisely and completely into the reaction flask for one hour, and then refluxing for two hours. And, 100 ml of acetonitrile with 74.2 g (0.36 mol) N-(2-bromoethyl)-azepine dissolved therein are dropwisely added into the reaction flask at the temperature of 70~80° C., and then 3 grams of sodium iodide are added therein for refluxing for 4 hours.

2. The solvent in the reaction flask is recovered under the pressure reduction situation, and the reaction flask is cooled to the temperature of 0° C. And, 150 ml of water and 200 ml of toluene are dropwisely added into the reaction flask to generate an aqueous layer and a toluene layer, such that 100 ml of toluene is added therein so as to extract the toluene layer. Then, the extracted toluene layer solution is collected for washing by 100 ml of ice water once time. Then, a predetermined amount of anhydrous $MgSO_4$ is added into the extracted toluene layer solution so as to dry out the water, and finally, 2 grams of activated carbon is added therein after. After decolorizing below the temperature of 20° C., HCl (g) is filled into the extracted toluene layer solution until having pH value of 2~3 so as to generate solid precipitated. Finally, a predetermined amount of acetone is added to the extracted layer solution for processing recrystallization so as to generate white L-setastine hydrochloride solid.

mp173~175° C. The yield of the reaction is 85%. ee99.2%, $[a]_D^{20}=-7.7°$ (c1.00, CH$_3$OH).

Embodiment 4

The Synthesis of L-Setastine Hydrochloride 1. 18 g (0.45 mole) of 60% sodium hydride and 100 ml of tetrahydrofuran are added into the reaction flask with nitrogen gas for stirring at the temperature of 50~55° C., and 50 ml of tetrahydrofuran with 51.3 g (0.3 mole) of R-chlorodiphenethyl alcohol dissolved therein is dropwisely and completely added therein for one hour, and then the reaction flask is in heat preservation for two hours. And, 120 ml of tetrahydrofuran with 107 g (0.36 mole) of p-toluene sulfonic acid 2-aza-cyclohexyl ester are added into the reaction flask, and then 1 gram of crown ether are added for refluxing for 6 hour.

2. The solvent in the reaction flask is recovered under the pressure reduction situation. 200 ml of toluene solution is added into the reaction flask and cool down until the temperature of 0° C., and then 100 ml of water is dropwisely added into the reaction flask to from a aqueous layer and a toluene layer, and finally 100 ml of toluene is added therein so as to extract the toluene layer. Then, the extracted toluene layer solution is collected for washing by 100 ml of ice water once time. Then, a predetermined amount of anhydrous MgSO$_4$ is added into the extracted toluene layer solution so as to dry out the water, and finally, 2 grams of activated carbon is added therein after. After decolorizing below the temperature of 20° C., HCl (g) is filled into the extracted toluene layer solution until having pH value of 2~3 so as to generate solid precipitated. Finally, a predetermined amount of acetone is added to the extracted layer solution for processing recrystallization so as to generate white L-setastine hydrochloride solid. mp173~175° C. The yield of the reaction is 85%. ee99.2%, $[a]_D^{20}=-7.7°$ (e1.00, CH$_3$OH).

Embodiment 5

The Synthesis Method of L-setastine Hydrochloride 1.76.1 g (0.5 moles) of DBU and 100 ml of dichloromethaneane are added into the reaction flask with nitrogen gas for stirring at the room temperature, and 60 ml of dichloromethane with 51.3 g (0.3 moles) of R-chlorodiphenethyl alcohol dissolved therein is dropwisely and completely added therein for 0.5 hour. And, 120 ml of dichloromethane with 131.2 g (0.4 mole) of 3-nitrobenzenesulfonate 2-azacyclohexyl ester are added into the reaction flask or refluxing for 6 hour.

2. The solvent in the reaction flask is recovered under the pressure reduction situation. 200 ml of toluene solution is added into the reaction flask and cool down until the temperature of 0° C., and then 100 ml of water is dropwisely added into the reaction flask to from a aqueous layer and a toluene layer, and finally 100 ml of toluene is added therein so as to extract the toluene layer. Then, the extracted toluene layer solution is collected for washing by 100 ml of ice water once time. Then, a predetermined amount of anhydrous MgSO$_4$ is added into the extracted toluene layer solution so as to dry out the water, and finally, 1 gram of activated carbon is added therein after. After decolorizing below the temperature of 20° C., HCl (g) is filled into the extracted toluene layer solution until having pH value of 2~3 so as to generate solid precipitated. (drain the solvent to generate solid precipitated.) Finally, a predetermined amount of acetone is added to the extracted layer solution for processing recrystallization so as to generate white L-setastine hydrochloride solid. mp173~175° C. The yield of the reaction is 82%. ee99.1%, $[a]_D^{20}=-7.6°$ (c1.00, CH$_3$OH).

Embodiment 6

The Synthesis Method of L-setastine Hydrochloride

1. The L-setastine hydrochloride can be synthesized by the SFC method. The Daicel chiral column setastine hydrochloride racemic (provided by Anhui Kelong medicine research institute) is used for chiral isomer separation by the Daicel preparation equipment, and its corresponding component is collected, so that pure optical isomers can be obtained by rotary evaporators. Column model for Daicel preparation equipment is CHIRALPAK AY-H (5 cm I.D.×25 cm L.), and the mobile phase is CO$_2$/EtOH/DEA=85/15/0.1 (v/v), and the flow rate is 100 g/min. The yield for the synthesis method is 40%, which means that 0.5 gram of L-setastine hydrochloride is obtained by adding 0.2 g of setastine hydrochloride racemic. The ee value is 98%, and $[a]_D^{20}=-7.4°$ (c1.00, CH$_3$OH). NMR results were as follows:

¾ (1H)-NMR (DMSO-d6, δ (ppm)): 1.56-1.65 (4H), 1.82-1.87 (4H), 1.87 (3H), 3.17-3.37 (4H), 3.32 (2H), 3.60 (2H), 7.20-7.41 (9H).

Meanwhile, 0.22 grams of D-setastine hydrochloride are obtained, which has the yield for generating D-setastine hydrochloride is 44%, and ee value thereof is 98.5%.

Embodiment 7

The Observation for the Mortality of Guinea Pigs after Taking Setastine Hydrochloride 1. Sample name: KL-001 (R-setastine hydrochloride prepared in embodiment 6), KL-002 (L-setastine hydrochloride prepared from embodiment 2, 3, 4, 5, or 6), and KL-003 (setastine hydrochloride racemic) provided by Anhui Kelong medicine research institute).

2. The specifications of content: There are three groups of each sample, which is high, medium, and small-dose group, wherein dosages for high, medium, small-dose group are 0.68 mg/kg, 0.32 mg/kg, and 0.16 mg/kg respectively. The dosages are considerable 20, 10, and 5 times comparing with the clinical dosages.

3. The preparation method for test sample: For the KL-001 sample, 84 ml of distilled water is added to KL-001 sample so as to obtain a large-dose group of KL-001, which is according to the gavage feeding volume of guinea pigs, which is 0.1 ml/100 g, which is the same as 0.68 mg/kg; and medium and small-does group of KL-001 are diluted by the high-dose group of KL-001 for double and quadruple times. For the KL-002 sample, 125 ml of distilled water is added to KL-002 sample to obtain a large-dose group of KL-002, which is according to the gavage feeding volume of guinea pigs, which is 0.1 ml/100 g, which is the same as 0.68 mg/kg; and medium and small-does group are diluted by the high-dose group for double and quadruple times. For KL-003 sample, 75 ml of distilled water is added to KL-003 sample so as to obtain a large-dose group of KL-003, which is according to the gavage feeding volume of guinea pigs, which is 0.1 ml/100 g, which is the same as 0.68 mg/kg; and medium and small-does group of KL-003 are diluted by the high-dose group of Kl-003 for double and quadruple times.

4. Animal Test:

Source: general level guinea pigs, license number: SCXK (Anhui) No. 2007-001, provided by Anhui Changlinhe Pharmaceutical Technology Co., Ltd.

Weight: 180~200 g.

Gender: 56 male guinea pigs and 56 female guinea pigs.

Number of animals: 112.

Feeding environment: The temperature of the environment is 20~26° C. The relative humidity is 40~70%. The environment is day and night alternatively with natural ventilation and mechanical ventilation equipment. Animal Use License No.: SYXK (Anhui) 2008-002.

Particulate forage and padding materials are provided by Anhui Changlinhe Pharmaceutical Technology Co., Ltd.

Drinking water: sterile water provided by Anhui medicine research institute and instrument Number for sterile drinking water for LAWS experimental animals is YQ-14.

5. Solvent and Instrument:

Histamine: provided by Shanghai Rouji Biological Technology Development Co., Ltd., and the batch number is 110531; and onetime injection.

6. Test Methods:

112 guinea pigs are fed in the feeding environment (to adapt in the environment) for three days, and are randomly divided into 10 groups, namely a control group, a high-dose group of KL-001, a medium-dose group of KL-001, a small-dose group of KL-001, a high-dose group of KL-002, a medium-dose group of KL-002, a small-dose group of KL-002, a high-dose group of KL-003, a medium-dose group of KL-003, and a small-dose group of KL-003. The dosage for high-dose group of Kl-001, KL-002, and Kl-003 is 0.68 mg/kg, and the dosage for medium-dose group of Kl-001, KL-002, and Kl-003 is 0.32 mg/kg, and the dosage for small-dose group of Kl-001, KL-002, and Kl-003 is 0.16 mg/kg, which are 20, 10, 5 times respectively comparing with the clinical dose. Each guinea pig from each group is fed by corresponding amounts of test sample for two days, which is according to the amount of 0.1 ml/100 g. Finally, each guinea pig is fed with lethal dose of histamine, which is 20 mg/kg after the last injection of test sample, and then observing the number of deaths of guinea pigs within 24 hours.

Experimental measurement data are collected by using SPSS11.0 software for statistical processing, and the results is displayed by $\bar{x} \pm S$, which is analyzed via a one-way ANOVA statistical methods.

Experimental results are shown below.

The death effect of the histamine for guinea pigs from each group of KL-001, KL-002 and KL-003.

| Group | Dose (mg/kg) | n | Number of death | Death Percentage (%) |
|---|---|---|---|---|
| Blank Control | — | 11 | 11 | 100 |
| Group KL-001 | 0.68 | 11 | 11 | 100 |
|  | 0.32 | 11 | 11 | 100 |
|  | 0.16 | 11 | 11 | 100 |
| KL-002 | 0.68 | 11 | 0 | 0 |
|  | 0.32 | 11 | 2 | 18 |
|  | 0.16 | 11 | 4 + 1 | 45 |
| KL-003 | 0.68 | 12 | 1 + 1 | 16 |
|  | 0.32 | 11 | 3 + 1 | 36 |
|  | 0.16 | 12 | 6 + 2 | 66 |

Comparing with the blank control group, the death percentages of the high, medium, small-dose group for KL-001 group (0.68 mg/kg, 0.32 mg/kg, 0.16 mg/kg) are 100%, so test sample Kl-001 doesn't has protective effect. The death percentages of the high, medium, small-dose group for KL-002 group (0.68 mg/kg, 0.32 mg/kg, 0.16 mg/kg) are 0%, 18%, and 45% respectively, wherein, in the small-dose group of KL-002, a guinea pig dies one day after taking the histamine. The death percentages of the high, medium, small-dose group for KL-003 group (0.68 mg/kg, 0.32 mg/kg, 0.16 mg/kg) are 16%, 36%, and 66% respectively, wherein there are one, one, and two guinea pig die in the second day after taking the histamine for the high, medium, and small-dose group (0.68 mg/kg, 0.32 mg/kg, 0.16 mg/kg) of KL-003 respectively, and the other guinea pigs die in that day.

The results show that for the sample KL-001 (D-setastine hydrochloride) doesn't has the protective effect on histamine-induced death for guinea pigs. For the test sample KL-002 (L-setastine hydrochloric) and KL-003 (setastine hydrochloride racemic), they have significant protective effect of histamine-induced death for guinea pigs, and the protective effect of KL-002 (L-setasine hydrochloride) is stronger than that of the KL-003 (setastine hydrochloride racemic).

Embodiment 8

The Preparation of L-setastine Hydrochloride Tablets

| Pharmaceutical formulations: the ratio of each ingredient | Dosage for each 1000 tablets |
|---|---|
| L-setastine hydrochloride | 1.1 g |
| Lactose | 62 g |
| Hydroxypropylcellulose | 1.4 g |
| 3% of hydroxypropyl methyl cellulose (HPMC) solution in ethanol | 16 ml |
| Magnesium Stearate | 0.5 g |

The preparation method of L-setastine hydrochloride tablets comprises the steps of:

1. seperatively crushing and then screening L-setastine hydrochloride, lactose (120 mesh), and hydroxypropylcellulose (HPC) through a 120 mesh sieve so as to mix them together and gradually increase amount in certain scale to obtain L-setastine hydrochloride mixture.

2. adding 3% of hydroxypropyl methyl cellulose (HPMC) solution in ethanol in the L-setastine hydrochloride mixture and then drying out the L-setastine hydrochloride mixture at the temperature of 60±5° C. so as to stabilize the size of the particles, wherein 3% of hydroxypropyl methyl cellulose (HPMC) solution in ethanol is a soft material, a binder, in a 20# nylon sieve wet granulation method.

3. mixing the dried particles with magnesium stearate.

4. testing the content and moisture within dried particles, and then tablet forming, full inspection, and packaging.

The above description is only a preferred embodiments of the present invention, and it should be noted that any person skilled in the art can modify and improve the present invention without departing from the spirit and scope thereof, wherein other embodiments, alternatives, modifications, equivalents, and applications without departing from the spirit and scope of the present invention is regarded as the protection scope of the present invention.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing a compound of L-setastine hydrochloride, comprising the steps of, (a) providing a compound of formula II having a formula of:

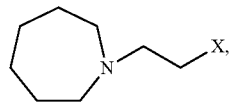

wherein the X is selected from a group consisting of Chlorine (Cl), Bromine (Br), Iodium (I), acyloxy, and sulfonyloxy;

(b) providing a compound of formula III having a formula of:

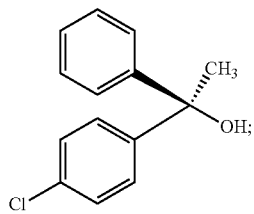 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said solvent is toluene solution.

2. A method for preparing a compound of L-setastine hydrochloride, comprising the steps of, (a) providing a compound of formula II having a formula of:

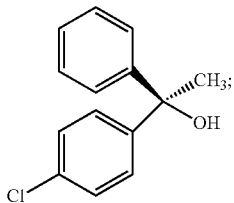

wherein the X is selected from a group consisting of Chlorine (Cl), Bromine (Br), Iodium (I), acyloxy, and sulfonyloxy;

(b) providing a compound of formula III having a formula of:

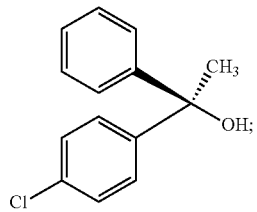 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said solvent is acetonitrile.

3. A method for preparing a compound of L-setastine hydrochloride, comprising the steps of, (a) providing a compound of formula II having a formula of:

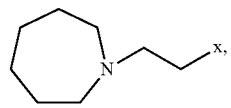

wherein the X is selected from a group consisting of Chlorine (Cl), Bromine (Br), Iodium (I), acyloxy, and sulfonyloxy;

(b) providing a compound of formula III having a formula of:

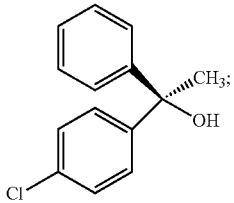 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said solvent is tetrahydrofuran.

4. A method for preparing a compound of L-setastine hydrochloride, comprising the steps of, (a) providing a compound of formula II having a formula of:

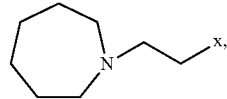

wherein the X is selected from a group consisting of Chlorine (Cl), Bromine (Br), Iodium (I), acyloxy, and sulfonyloxy;

(b) providing a compound of formula III having a formula of:

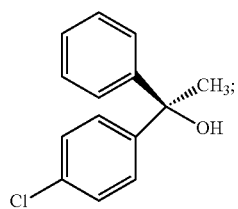 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said solvent is dichloromethaneane.

5. A method for preparing a compound of L-setastine hydrochloride, comprising the steps of, (a) providing a compound of formula II having a formula of:

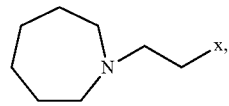

wherein the X is selected from a group consisting of Chlorine (Cl), Bromine (Br), Iodium (I), acyloxy, and sulfonyloxy;

(b) providing a compound of formula III having a formula of:

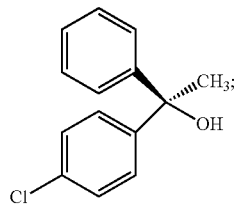 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said alkali-based compound is sodium tert-butoxide.

6. A method for preparing a compound of L-setastine hydrochloride, comprising the steps of, (a) providing a compound of formula II having a formula of:

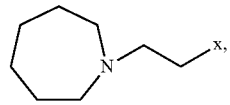

wherein the X is selected from a group consisting of Chlorine (Cl), Bromine (Br), Iodium (I), acyloxy, and sulfonyloxy;

(b) providing a compound of formula III having a formula of:

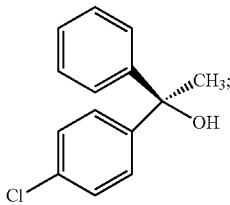 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said alkali-based compound is sodium hydride.

7. A method for preparing a compound of L-setastine hydrochloride, comprising the steps of, (a) providing a compound of formula II having a formula of:

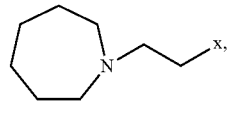

wherein the X is selected from a group consisting of Chlorine (Cl), Bromine (Br), Iodium (I), acyloxy, and sulfonyloxy;

(b) providing a compound of formula III having a formula of:

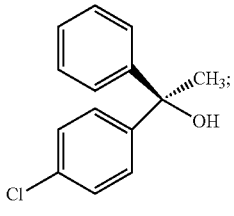

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said alkali-based compound is 1, 8-Diazabicyclo [5.4.0]undec-7-ene (DBU).

8. A method for preparing a compound of L-setastine hydrochloride, comprising the steps of, (a) providing a compound of formula II having a formula of:

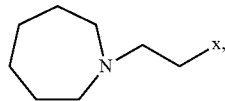

wherein the X is selected from a group consisting of Chlorine (Cl), Bromine (Br), Iodium (I), acyloxy, and sulfonyloxy;

(b) providing a compound of formula III having a formula of:

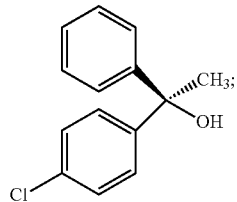 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein a catalyst is provided to support the reaction between said formula II and formula III, wherein said catalyst is polyethylene glycol.

9. A method for preparing a compound of L-setastine hydrochloride, comprising the steps of, (a) providing a compound of formula II having a formula of:

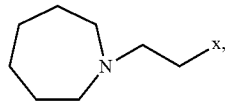

wherein the X is selected from a group consisting of Chlorine (Cl), Bromine (Br), Iodium (I), acyloxy, and sulfonyloxy;

(b) providing a compound of formula III having a formula of:

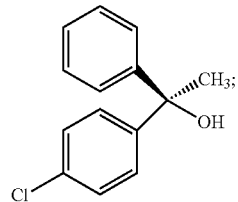

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein a catalyst is provided to support the reaction between said formula II and formula III, wherein said catalyst is crown ether.

10. A method for preparing a compound of L-setastine hydrochloride, comprising the steps of, (a) providing a compound of formula II having a formula of:

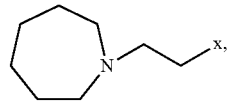

wherein the X is selected from a group consisting of Chlorine (Cl), Bromine (Br), Iodium (I), acyloxy, and sulfonyloxy;

(b) providing a compound of formula III having a formula of:

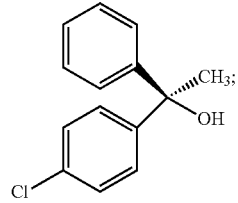 [SMILES: C[C@@](O)(c1ccccc1)c1ccc(Cl)cc1]

and (c) reacting said compound of formula II with said compound of formula III in absence of air or in presence of air and an environment of alkali-based compound, and in a solvent under a solvent reflux temperature for 4 to 6 hours to obtain said compound of L-setastine hydrochloride;

wherein said L-setastine hydrochloride is analyzed by a NMR instrument.

* * * * *